(12) United States Patent
Bracht

(10) Patent No.: US 6,689,379 B1
(45) Date of Patent: Feb. 10, 2004

(54) TRANSDERMAL THERAPEUTIC SYSTEM WITH NEUTRALIZED ACRYLIC ADHESIVE PATCH

(75) Inventor: Stefan Bracht, Ochtendung (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 09/959,288

(22) PCT Filed: Apr. 7, 2000

(86) PCT No.: PCT/EP00/03112
§ 371 (c)(1),
(2), (4) Date: Oct. 19, 2001

(87) PCT Pub. No.: WO00/64418
PCT Pub. Date: Nov. 2, 2000

(30) Foreign Application Priority Data

Apr. 22, 1999 (DE) .......................... 199 18 106

(51) Int. Cl.⁷ .................. A61F 13/02; A61F 13/00; A61L 15/16
(52) U.S. Cl. .................. 424/448; 424/449; 424/443
(58) Field of Search ............... 424/448, 449

(56) References Cited

U.S. PATENT DOCUMENTS 4,880,416 A * 11/1989 Horinchi et al.
5,876,745 A    3/1999 Muraoka et al.

FOREIGN PATENT DOCUMENTS

| DE | 279 611 A1 | 6/1990 |
| DE | 43 10 012 A1 | 9/1994 |
| DE | 44 23 850 A1 | 1/1996 |
| DE | 44 29 791 A1 | 2/1996 |
| DE | 196 53 605 A1 | 6/1998 |
| DE | 197 28 516 A1 | 1/1999 |
| EP | 0 387 751 A2 | 9/1990 |
| EP | A0394956 | 10/1990 |
| EP | 0 446 636 * | 9/1991 |
| EP | A0446636 | 9/1991 |
| JP | 52-59636 | 5/1977 |
| WO | 99 49852 | 10/1999 |

* cited by examiner

Primary Examiner—Thurman K. Page
Assistant Examiner—Isis Ghali
(74) Attorney, Agent, or Firm—Birch, Stewart, Kolasch & Birch, LLP

(57) ABSTRACT

A transdermal therapeutic system embodied as a matrix or reservoir system is characterized by
  a content of at least one basic- or neutral-reacting pharmaceutical active agent
  a content of a pressure-sensitive adhesive polymer which possesses as part of its chain acrylic acid or methacrylic acid units, the content of the carboxyl groups, relative to the mean polymer mass, being 0.5 to 10.0% (w/w) and the carboxyl groups being present stoichiometrically at 5 to 100 %, preferably 10 to 50%, in form of alkali salts or alkaline earth salts.

Water-binding additives may also be present, for reducing the sensitivity to moisture.

33 Claims, 3 Drawing Sheets

TRANSDERMAL THERAPEUTIC SYSTEM WITH NEUTRALIZED ACRYLIC ADHESIVE PATCH

This application is the national phase under 35 U.S.C. §371 of PCT International Application No. PCT/EP00/03112 which has an International filing date of Apr. 7, 2000 which designated the United States of America.

FIELD OF THE INVENTION

This invention relates to the chemical neutralization of pressure-sensitive adhesive polymers or copolymers containing acrylic acid or methacrylic acid incorporated in their polymer chains.

BACKGROUND OF THE RELATED ART

Polymers based on acrylic acid or methacrylic acid and on esters thereof are of particular importance among pressure-sensitive adhesives since they are not only backbone builders and are frequently the main component of a pressure-sensitive adhesive formulation, but also possess pressure-sensitive adhesive qualities themselves. This constitutes a fundamental difference to mixtures of natural or synthetic rubbers (backbone builders) with natural or synthetic resins (so-called tackifiers), for example. With polyacrylate-based pressure-sensitive adhesives there is no necessity of adding low-molecular components in order to provide them with pressure-sensitive adhesive properties. Besides the manifold possibilities for technical application, the latter quality renders the pressure-sensitive polyacrylate adhesives particularly attractive for medicinal use in humans or animals. Low-molecular components—mostly resins, as required as tackifying additives to rubbers—can cause irritation and even allergic reactions when absorbed via the skin. This risk is for the most part non-existent in polyacrylates, which is why these are also described as "hypoallergenic" in medicinal use.

Pressure-sensitive polyacrylate adhesives are today widely used in the production of medicinal patches for wound treatment or fixation in medicinal operations (key word "adhesive patch"). Furthermore they represent the most significant group of pressure-sensitive adhesives used for making transdermal therapeutic systems (TTSs).

Apart from their good skin compatibility, the reasons therefor lie in the following properties:

Polyacrylates can be composed in manifold ways from a large selection of monomers. In this way, it is possible to adjust the pressure-sensitive adhesive properties of the polymers and their affinity to the surfaces which are to be bonded, e.g. human skin, within broad limits. In this connection, it is, in particular, the chemical nature of the lateral chains on the polyacrylate backbone which plays a crucial part. The lateral chains not only determine hydrophilia-lipophilia balance within the polymer, and thus, for example, the amount of moisture that can be absorbed: by means of appropriate lateral chains and the mixture thereof it is, in particular, possible to reduce the crystallinity of the polymer. A reduction of the crystallinity and thereby of the glass transition temperature has a positive effect on the pressure-sensitive adhesive properties of the polymer by promoting the flowability and thereby the quick wetting of the surfaces. For medicinal applications of TTSs a low glass transition temperature is of particular importance: In the non-crystalline state, the polymer, that is, its side chains are particularly permeable to pharmaceutic active substances and auxiliaries contained. This is essential for the quick release at the site of application.

Polyacrylates possess a high solubility for most pharmaceutic active substances. Typically, it is higher than in other pressure-sensitive adhesives suitable for the production of TTSs such as, for instance, natural rubber-resin mixtures, or in pressure-sensitive silicone adhesives. Frequently, the required quantities of an active substance can actually be dissolved—and thereby incorporated in a TTS in the form most suitable for delivery—in polyacrylates only. When polymerising unesterified acrylic or methacrylic acid in polyacrylates, the latter can carry free carboxyl groups on their chain. These carboxyl groups are suitable for later connecting several polymer chains with each other via the groups. Typical reagents which are generally known to those skilled in the art are organometallic complexes such as, for example, aluminium or titanyl acetyl acetonate. These introduce polyvalent cations into the polymer, which cations then simultaneously bind to several carboxyl groups on different polymer chains. In this way, it is possible to crosslink linear polymer chains three-dimensionally. Typically, this takes place when heating and drying the corresponding polymer solution in the course of processing to yield the final product. Other possibilities of crosslinking result from irradiation of high-energy quanta of light, e.g. UV radiation, in combination with suitable crosslinking reagents. Crosslinking prevents the flowability of the polymer mass while maintaining a deformability which has remained essentially elastic only. When crosslinking is dispensed with, typically there occurs an unwanted slow flow—known as "cold flow"—of the pressure-sensitive adhesive under action of any outer force, in the most simple case: gravity. Upon application on the skin, cold flow can lead to the pressure-sensitive adhesive penetrating the pores of the skin more deeply than wanted, and thereby make removal more difficult, and thus painful. Here, too, the capacity for crosslinking affords corresponding advantages. It is thus one of the most important qualities of polyacrylates.

Polyacrylates are obtained from polymerisation of the vinyl residue of acrylic or methacrylic acid. This mechanism enables in a very simple manner the incorporation of foreign monomers (non-(meth)acrylates), which likewise contain an ethylenically unsaturated molecule part. These are, for example, ethylene, vinyl acetate or other esters of vinyl alcohol, and especially various vinyl pyrrolidones, as well as styrene and crotamiton. In the field of medicinal pressure-sensitive adhesives one finds, for example, numerous mixed polymers with vinylpyrrolidones. These enable the adjustment of higher solubilities of certain active substances, or also of higher moisture absorption or moisture tolerance on the skin as application site.

Altogether, not only in the field of technical applications do polyacrylates represent an indispensable group of pressure-sensitive adhesives. In particular in medicinal application, polyacrylates are of outstanding importance due to the sum of their positive properties in combination with their being available at low cost.

SUMMARY OF THE INVENTION

The present invention relates to the chemical modification of acid polyacrylate pressure-sensitive adhesives. The term acid polyacrylate pressure-sensitive adhesives means polymers possessing the following properties:

the polymer has pressure-sensitive adhesive properties at room temperature relative to the mean polymer mass, at least 50% (w/w) thereof are monomers from the group of acrylic or methacrylic acid or ester derivatives thereof relative to the mean polymer mass, 0.5% (w/w), but at maximum 10% (w/w) thereof, are unesterified acrylic or methacrylic acids.

DETAILED DESCRIPTION

Figure 1:
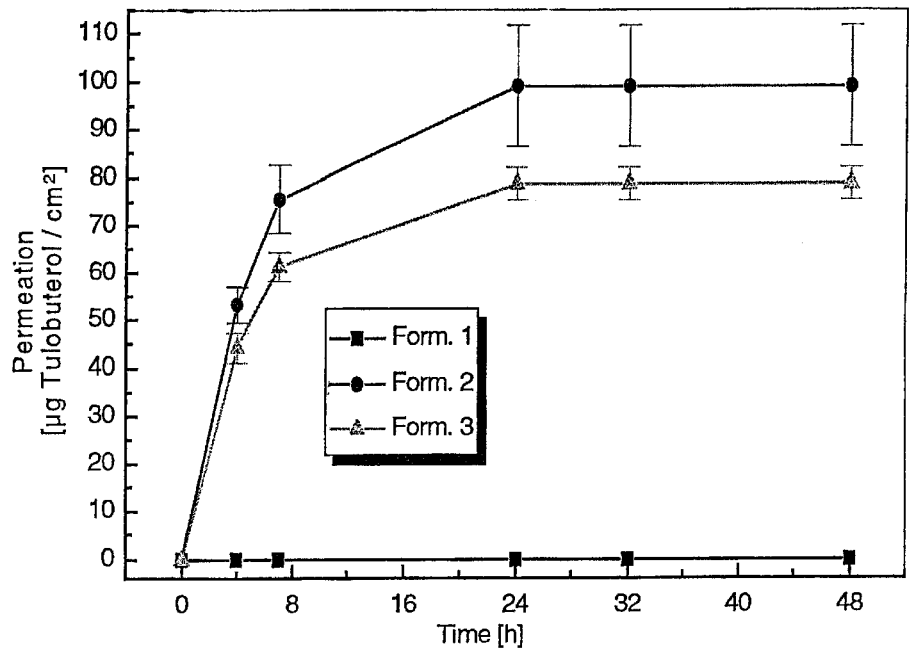
FIG. 1 is a graph of the permeation of tulobuterol.

The object, of the present invention was to improve the acid polyacrylate pressure-sensitive adhesives' water absorptivity as well as their tolerance of moisture in general.

This is desirable, in particular, in the medicinal treatment of humans or animals, since the pressure-sensitive adhesives positioned on the skin are subjected to the continuous release of water vapour by the skin and, in humans, also to the moisture produced by sweating. Under these conditions, the pressure-sensitive adhesive properties are frequently diminished considerably, so that a medicinal patch will prematurely become detached from the skin. With conventional acid polyacrylate pressure-sensitive adhesives, problems may occur already when sticking the medicinal patch onto moist skin. Moisture absorptivity constitutes a desirable improvement in yet a further context: In transdermal therapeutic systems, a pharmaceutical active agent is typically contained in the pressure-sensitive adhesive layer. Such active agents are mostly lipophile substances, which are frequently highly soluble in polyacrylates. Good solubility in the adhesive matrix is, however, detrimental to the release of active substance to the application site. The uptake of moisture in the pressure-sensitive adhesive matrix at the site of application (water vapour, sweat) can diminish the solubility of lipophile active agents in said matrix. An increased capacity for moisture absorption thus has a positive effect on the release of many lipophile active substances from a pressure-sensitive polyacrylate adhesive.

A further object of the invention was to improve the active substance release of basic active substances from acid, pressure-sensitive adhesive acrylate copolymers. Frequently, the release of basic active substances from such polymers is considerably reduced or delayed by chemical acid-base interaction, so that this combination is practically only little useful for developing a TTS which is to possess a release rate of active substance to the skin that is to be as high as possible.

The above-described object is achieved according to the invention in that the carboxyl groups contained in acid polyacrylate pressure-sensitive adhesives are partially or completely neutralized by converting them to the alkali salts or alkaline earth salts. As reagents are used alkaline compounds of the alkali metals or alkaline earth metals, preferably their hydroxides such as sodium or potassium hydroxide. The resultant polymer salts possess—as is the nature of all ionically charged molecules or molecule parts—a high binding capacity for water in the form of hydrate covers. Especially the counter ions sodium and potassium are capable of binding a large amount of water in this manner.

Neutralizing or neutralization means to convert the acidically reacting carboxyl groups present into salts by reacting them with a base. Neutralization means the complete conversion of all acid groups in this way. The neutralization degree, as percentage, expresses at what proportion the conversion has taken place as against the theoretically possible, complete conversion.

A neutralization degree of more than 100% should be avoided since the system of alkali carboxylate and excessive alkali does not form a buffer, but can form a highly alkaline and thus chemically decomposing medium. A neutralization degree of more than 100% may, however, be useful if other acid components are contained in the formulation, as, for instance, low-molecular carboxylic acids, sulfonic acids or fatty acids. Such substances can be found among plasticizers, tackifiers or enhancers.

Achieving the above object was possible by utilizing—instead of the aqueous solutions of sodium or potassium hydroxide used in most cases—the corresponding alcoholic, preferably methanolic or ethanolic solutions, optionally containing a low content of water. Under these conditions the reaction can be carried through in an environment in which the above-described acid polyacrylate pressure-sensitive adhesives do not precipitate from the solution and in which the products also remain stably dissolved.

Also possible is the use of alkali alcoholates, e.g. sodium ethanolate or potassium ethanolate. These alkaline reagents make the use of water in the neutralization reaction completely redundant, and no water is formed as a product either.

"Low content of water" means, with reference to alcoholic solutions, that the volume fraction of water in the reagent solution does not exceed 20% and, in particular, does not exceed 10%. Ideally, water-free solutions are used.

According to the prior art, pressure-sensitive polyacrylate adhesives the carboxyl groups of which are converted into salts by alkalis or at least convertible into salts in an alkaline medium are typically used in the field of water-dispersible preparations. If the number of carboxyl groups in the polymer is large enough, hydrophilia can be increased by the conversion of carboxyl groups into salts to such an extent that the product can be processed dispersed in water.

If the content of carboxyl groups in the polymer is increased further, it is even possible to achieve solubility in an alkaline aqueous environment.

In contrast thereto, the herein-described polyacrylates comprise only a small content of carboxyl groups. This content is not sufficient to render the neutralized product water-soluble or water-dispersible. Such dispersibility or solubility in water is in fact not desirable for application on the skin since otherwise detachment can take place already due to skin perspiration.

In the field of technical and medicinal pressure-sensitive adhesives there are also described polyacrylates which likewise possess only a small content of 0.05% to 8.0% (w/w) of carboxyl group-containing monomers, these monomers being present partially or completely as alkali salt. The advantages were seen in good cohesion, good weathering and ageing resistance, as well as when wearing the patch on perspiring skin. However, no observations are available here as to possible modifications of the delivery of pharmaceutical active agents from such matrices.

A quite similar case is JP 52-059636 A, which likewise provides for a content of akali-reacting alkali metal compounds to be contained in a pressure-sensitive polyacrylate adhesive having a small content of carboxyl groups. In addition, ionic crosslinking is provided. Here, too, there are no observations available as to possible modifications of the release of pharmaceutical active agents from such matrices.

The technique of neutralizing polyacrylate pressure-sensitive adhesives has also been used in conjunction with carboxyl group-containing pharmaceutical active substances. Here, an increase of cohesion was achieved, under addition of larger amounts of plasticizing auxiliary substances, and especially the skin compatibility of the patch was improved by means of the active substance ibuprofene. The latter is seen in connection with raising the pH towards physiological values of the skin surface. Otherwise, patches comprising a carboxyl group-containing pharmaceutically active agent could react too acidically, and thereby cause irritation. Within the group of possible pharmaceutical active agents, however, only such active agents are discussed which contain carboxyl groups in the molecule and which can thus react acidically.

Increase of cohesion, improvement of adhesive properties and of the resistance to moisture, increase of the load-ability with plasticizing auxiliary substances, as well as the irritation-reducing effect in conjunction with acid pharmaceutical active substances have all been known as effects of neutralization of acid polyacrylate pressure-sensitive adhesives.

Surprisingly, it was found in connection with the present invention that especially the use of basic pharmaceutical active substances in combination with neutralized acid polyacrylate pressure-sensitive adhesives results in an, in part extraordinary, increase of the release rate of the pharmaceutical active agent. Further, there is an entirely unexpected controllability of the release rate of basic pharmaceutical active agents by way of the neutralization degree of the acid polyacrylate pressure-sensitive adhesive.

The advantages resulting from such a combination in the field of transdermal therapeutic systems by far surpass the advantages already known as described above. Furthermore, it was found completely unexpectedly that there was also an improvement of the release of pharmaceutical active substances which react chemically neutral.

For basic pharmaceutically active agents it is in principle to be expected that the release of an acid polyacrylate pressure-sensitive adhesive will be impeded due to the formation of a reversible bond to the polymer by acid-base reaction. Though it is to be expected that neutralization of the polymer leads to the loosening of this bond, the extent of this effect, and especially the practically linear controllability thereof which has been observed, by far exceeds the expectations held by those skilled in the art.

With pharmaceutical active agents which react in a chemically neutral manner, no interaction with acid polyacrylate pressure-sensitive adhesives of the acid-base reaction type is to be expected at all. The improvement of the release behaviour which has nevertheless been surprisingly observed is possibly related to changes in the three-dimensional polymer structure and the solubility for low-molecular active substances embedded therein.

In addition to the already known positive effects of neutralization of acid polyacrylate pressure-sensitive adhesives, among which the increase of cohesion and thus the improvement of resistance to plasticizers play the most important part, there is thus a positive effect which has so far been unknown with respect to basic and neutral pharmaceutic active substances. This results in the subject-matter of the present invention being, in particular, novel transdermal therapeutic systems for the delivery of basic or neutral pharmaceutic active agents, based on neutralized pressure-sensitive polyacrylate adhesives.

Basic pharmaceutical active substances are those substances possessing as part of their molecular structure at least one group which is capable of chemically reacting as a Lewis base. Preferably, such groups are primary, secondary or tertiary aliphatic or aromatic amines. But they can also be basic-reacting amides, or guanidine structures. Examples are nicotine, tulobuterol or rivastigmine.

"Neutral" are such pharmaceutical active agents which cannot be converted into a pharmaceutically acceptable salt form, either by bases or acids. These are, for instance, steroid active substances such as testosterone, norethisterone acetate or estradiol as well as organic esters of nitric acid, especially nitroglycerine and isosorbide mononitrate or dinitrate.

Due to the high cohesion of neutralized pressure-sensitive polyacrylate adhesives, such formulations are particularly suited for incorporating liquid active substances or auxiliary substances, especially enhancers, in larger quantities of 10 to 80% (w/w), preferably 10 to 50% (w/w), relative to the adhesive matrix.

Owing to the high cohesion and low flowability of the neutralized pressure-sensitive adhesive films, however, spontaneous tack on the skin may lessen, so that such films do not always exhibit optimal adhesive properties. In such cases it can be required to provide, on the side facing the skin, a separate pressure-sensitive adhesive layer improving the adhesion of the system to the skin. This layer can in principle be composed of any pressure-sensitive adhesives that are suitable for medicinal application. Preferably, it should not markedly reduce the release of the pharmaceutic active substance from the layer of the neutralized polyacrylate matrix. To this end, it should in any case be made as thin as possible. Polymers suitable for the formation of the skin-facing pressure-sensitive adhesive layer are from the group of polyacrylates, silicone rubber, polyisobutylene, polyisoprene, as well as styrene-isoprene-styrene block copolymers and styrene-butadiene-styrene block copolymers.

The pressure-sensitive adhesive films of neutralized acrylate copolymers, especially those containing a high portion of unesterified acrylic or methacrylic acid in the polymer (3 to 10% w/w relative to the mean polymer mass) and having a high degree of neutralization (70 to 100%), proved to be too sensitive to moisture when worn on the skin for a prolonged period of time. This can result in a premature diminishment of adhesive power or in premature detachment from the skin surface, as compared to the non-neutralised form of the same pressure-sensitive adhesives.

This leads to an unwanted susceptibility of the TTSs to skin perspiration, combined with a diminished suitability for long-term use, for example, for at least 16 h. This can be of disadvantage especially for TTSs with long-term action (for 24 h or in the case of so-called two-day- or three-day-patches).

The problem of sensitivity to moisture could, however, be counteracted by admixing strongly water-absorbent additives. Suitable additives, which are capable of adsorbing large amounts of water without becoming dissolved therein, are pharmaceutically acceptable swelling agents, preferably sodium or calcium salts of crosslinked carboxymethyl cellulose (croscarmellose), sodium or calcium salts of crosslinked polyacrylic acid or crosslinked polyvinyl pyrrolidone (crospovidone).

Further examples are products such as galactoglucomannan, cellulose products, tragacanth, polyglycoside, fine-powdered polyamide, water-soluble polyacrylamide, carboxyvinyl polymerisate, agar-like algae products, mixed polymers from methyl vinyl ether and maleic acid anhydride, guar gum, hydroxypropyl guar gum or guar flour, gum arabic, dextrin and dextran, microbiologically produced polysaccharide gum such as the polysaccharide B 1459 or the highly water-soluble type keltrol, or synthetically produced polysaccharides such as the product ficoll, methyl glucose derivatives, hydroxymethyl propyl cellulose, polygalacturonic acid derivatives such as pectin or the amidated product pectinamide.

Of these, galactoglucomannan and microcrystalline cellulose are particularly preferred.

The swelling number of such substances, determined according to the European Pharmacopeia 1997, should be at least 2, but preferably above 4. The particle size should be 1 to 50 μm, but preferably 5 to 25 μm. This ensures that the liquid solutions of adhesive containing such substance can be coated without problems also with small layer thicknesses of at least 100 to 1000 μm.

The added amount of water-binding agent should be kept as low as necessary, since the volume occupied by this agent in the TTS is generally lost for the loading with active substance. Amounts from 0.1 to 5%-wt. (relative to the total weight of the active substance-containing, pressure-sensitive adhesive polymer film) of such a water-binding additive are generally sufficient for this purpose.

The invention will be illustrated in the following by way of embodiment examples.

Examinations on the thermodynamics of a model of ethylene vinyl acetate (EVA) copolymer film permeation For three basic pharmaceutical active agents, the release behaviour from an acid polyacrylate pressure-sensitive adhesive film in dependence from the neutralization of the adhesive and from the reagent used for this purpose was examined. All tests on EVA membrane were carried out with n=3 samples.

To this end, the active substance-containing pressure-sensitive adhesive films were stuck on an EVA film as carrier membrane, and the amount of active agent released over time through this membrane to an aqueous medium buffered to pH 5.5 and located on the opposite side was quantified by appropriate HPLC methods. Compared to biological membranes such as skin, EVA film has the advantage of high standardizability, so that extremely meaningful comparative measurements are possible. The permeation device was a modified permeation cell according to Franz as generally known in the field of TTS development. The use of EVA film as membrane in this test design enables the isolated observation of the thermodynamic activity of an active substance in the pressure-sensitive adhesive matrix. Since in the embodiment examples the active substance represents the only component which is low-molecular and capable of migration, it is the tendency of exclusively this active substance to exudate from the polymer matrix of the pressure-sensitive adhesive and to migrate into the acceptor medium after passing through the EVA membrane which is recorded.

Independently of the permeation properties of human skin for such an active substance, the release tendency of the system in respect of the active substance as measured here is the most essential impetus for transdermal therapy by means of such a system.

The TTSs tested were all composed of an active substance-containing pressure-sensitive adhesive layer having a weight per unit area of 80 g/m$^2$. The content of active substance in the case of tulobuterol, rivastigmin and xanomeline was 5% (w/w), in the case of testosterone 2.5% (w/w). To prepare the TTSs, the commercially available pressure-sensitive adhesive solution Durotak® 387-2051 (by National Starch), was mixed possibly with a 10% (w/w) methanolic solution of the alkali hydroxide in an amount corresponding to a neutralization degree of the polyacrylate of 100%. Only thereafter was the active substance added and dissolved in the mass. This solution was coated onto a siliconized carrier film of polyethylene terephthalate (PET) and dried in a drawing-off air oven for 10 minutes at 80° C. until a film was formed. The dry film was covered with a 15-μm-thick PET film.

Appropriate punched pieces were taken from this laminate, and the carrier film was removed before the active substance-containing film was stuck to the EVA carrier film.

TABLE 1

Formulations for EVA permeation.

| Formul. No. | Active Agent | Neutralizing Reagent | Neutralization Degree [%] |
|---|---|---|---|
| 1 | Tulobuterol | — | 0 |
| 2 | Tulobuterol | KOH | 100 |
| 3 | Tulobuterol | NaOH | 100 |
| 4 | Rivastigmin | — | 0 |
| 5 | Rivastigmin | KOH | 100 |
| 6 | Rivastigmin | NaOH | 100 |
| 7 | Xanomeline | — | 0 |
| 8 | Xanomeline | KOH | 100 |
| 9 | Xanomeline | NaOH | 100 |
| 10 | Rivastigmin | KOH | 20 |
| 11 | Rivastigmin | KOH | 40 |
| 12 | Rivastigmin | KOH | 60 |
| 13 | Rivastigmin | KOH | 80 |
| 14 | Testosterone | KOH | 0 |
| 15 | Testosterone | KOH | 50 |
| 16 | Testosterone | KOH | 100 |

NaOH = sodium hydroxide; KOH = potassium hydroxide

Example No. 17 with Nicotine as Active Substance

This example shows a two-layer matrix TTS with the basic active substance nicotine. The neutralized acrylate copolymer pressure-sensitive adhesive layer contains a water-binding additive (a so-called hydroabsorbent, in this special case: croscarmellose sodium, i.e. the sodium salt of crosslinked carboxymethyl cellulose). For a wearing period of 24 hours the finished TTS adhered perfectly, without any detachment from the skin.

The polymer solution for the first matrix layer has the composition according to Table 2. This solution is coated flatly, with a weight per unit area of 54 g/μm$^2$, onto a film of polyethylene terephthalate (19 μm PET), using an application unit. This coating product is immediately thereafter laminated with a pressure-sensitive adhesive layer of the composition according to Table 3 and having a layer thickness of 144 g/m$^2$.

This lamination product is heated for 10 minutes to 60° C., before coiling it to a rolled product. The rolled product is immediately, or after intermediate storage, processed in a conventional manner by longitudinal cutting and punching to form TTSs.

TABLE 2

| Description | Amount [%] | Function |
|---|---|---|
| Nicotin | 32.41 | basic active substance |
| Eudragit ® EPO | 27.00 | thickening polymer |
| Miglyol ® 812 | 40.23 | co-solvent |
| Vitamin E | 0.36 | antioxidant |

TABLE 3

| Description | Amount [%] | Function |
| --- | --- | --- |
| Durotak 387-2051 | 95.18 | acrylate copolymer pressure-sensitive adhesive |
| KOH | 0.77 | neutralization reagent |
| Aluminium acetyl acetonate | 0.05 | crosslinking reagent for the acrylate copolymer Durotak |
| croscarmellose sodium | 4.00 | hydroabsorbent |

The layer of adhesive according to Table 3 is prepared in a conventional, solvent-containing coating process with subsequent drying. Process solvents are ethyl acetate, methanol and acetyl acetone. The indicated quantity portions relate to the content in the dried layer.

Through diffusion, the liquid components of the first matrix layer (such as, for example, the active substance and the co-solvent) migrate into the matrix layer, which is initially free of active substance. After a few days this process is, however, completed and the finished TTS is ready for use.

Figure 2:
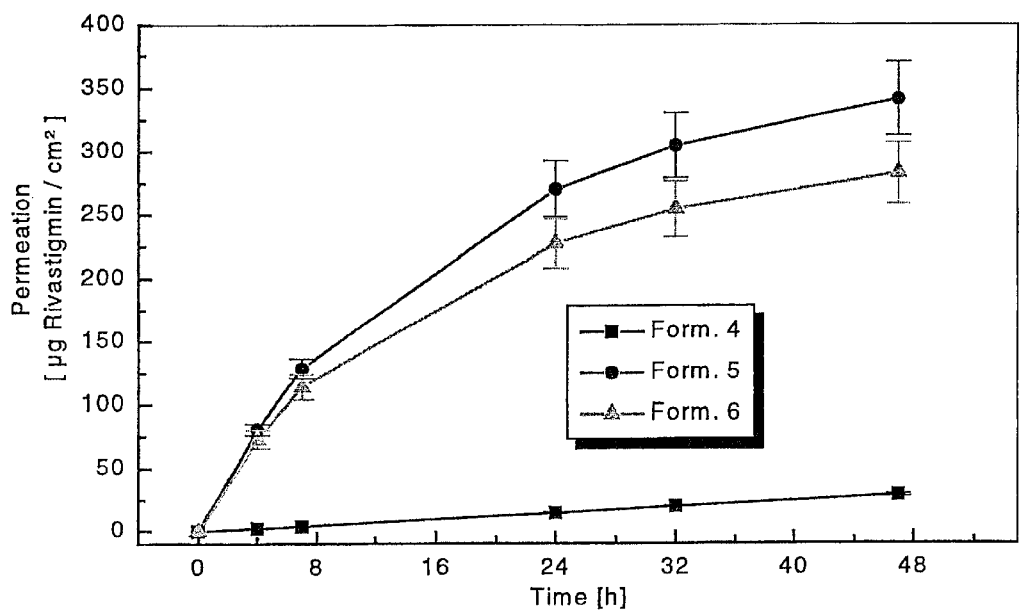
FIG. 2 is a graph showing the permeation of rivastigmin.
Figure 3:
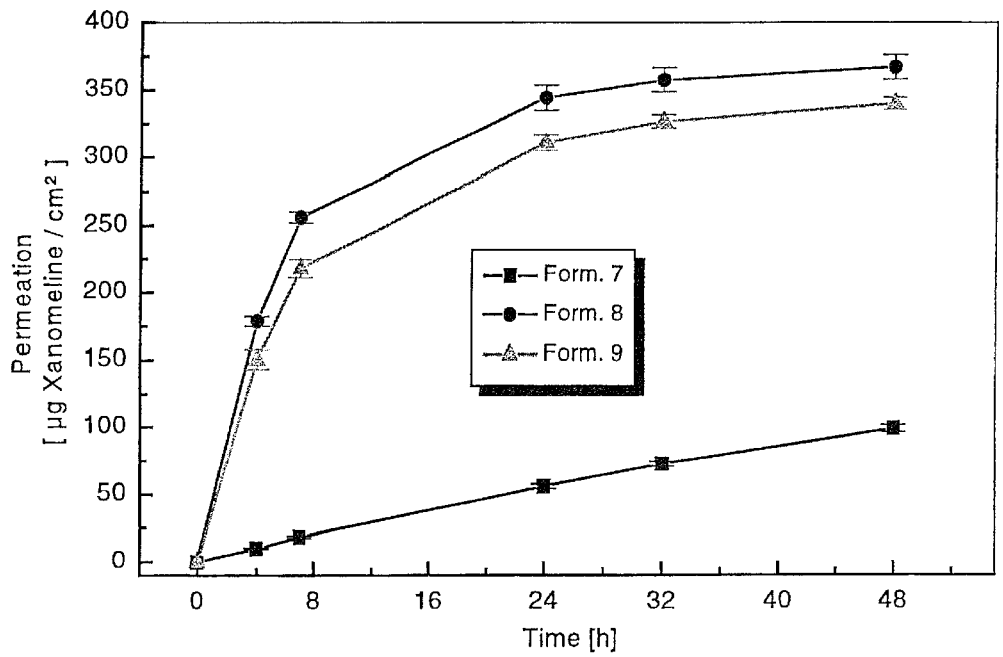
FIG. 3 is a graph showing the permeation of xanomeline.

FIGS. 1 to 3 show an extreme increase in the release of the three examined basic active substances of Examples 1 to 16 from the pressure-sensitive adhesive matrix if the polyacrylate is present in neutralized form. Furthermore, one can see a clear advantage of the use of potassium hydroxide over sodium hydroxide. As regards this effect it can only be assumed that it is related, in a way as yet unknown, to the larger ionic radius of potassium ions.

Figure 4:
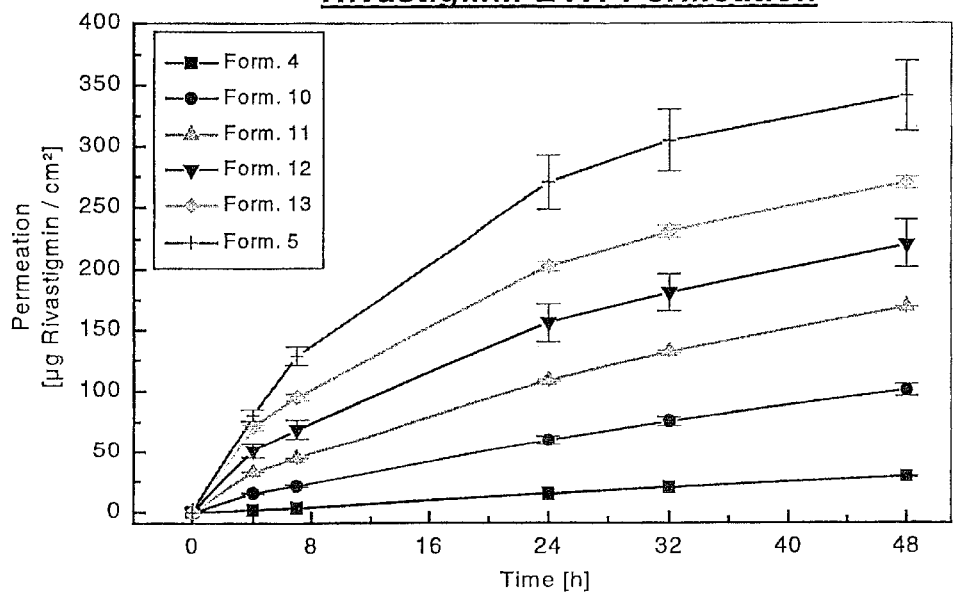
FIG. 4 is a graph showing the permeation of rivastigmin.

FIG. 4 shows the strong dependence of the effect from the neutralization degree for the case of rivastigmin as active substance by way of example.

Figure 5:
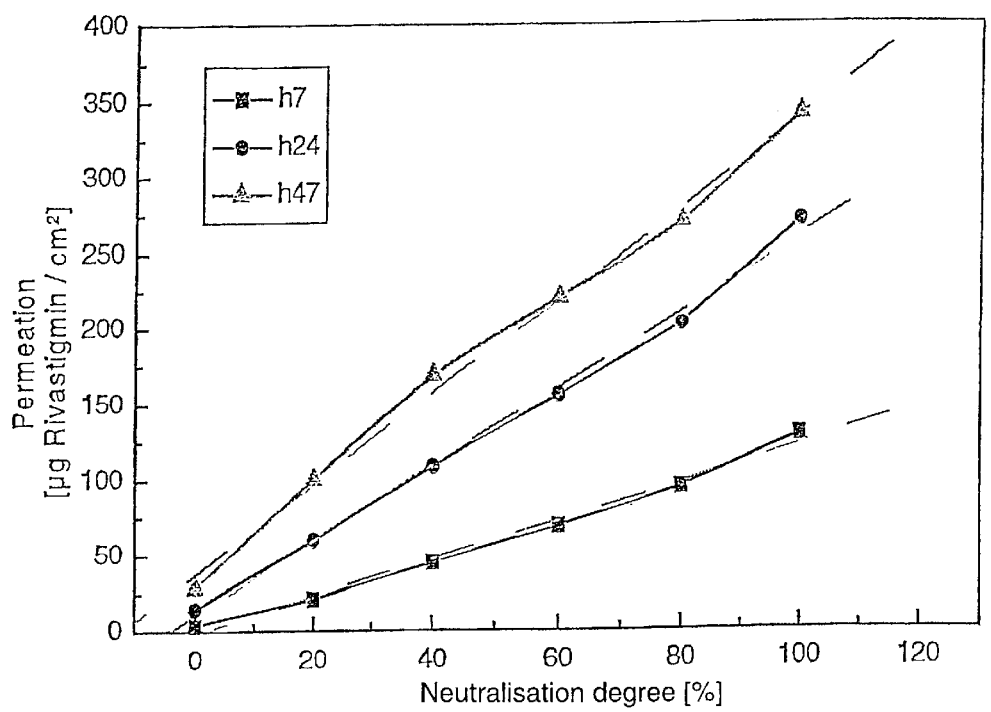
FIG. 5 is a graph showing the permeation of rivastigmin.

FIG. 5 shows the same data as FIG. 4 but with the permeated active substance amount plotted directly against the neutralization degree (note: neutralization degrees of 0 to 100% correspond to formulations 4, 10, 11, 12, 13, 5, in this order). This very suprisingly shows that practically throughout the entire range of neutralization degrees from 0 to 100% there exists a linear dependence. This dependence is illustrated by linear regressions represented as broken lines. The amount of active substance to be released per time can thus be exactly controlled by means of the neutralization degree.

Figure 6:
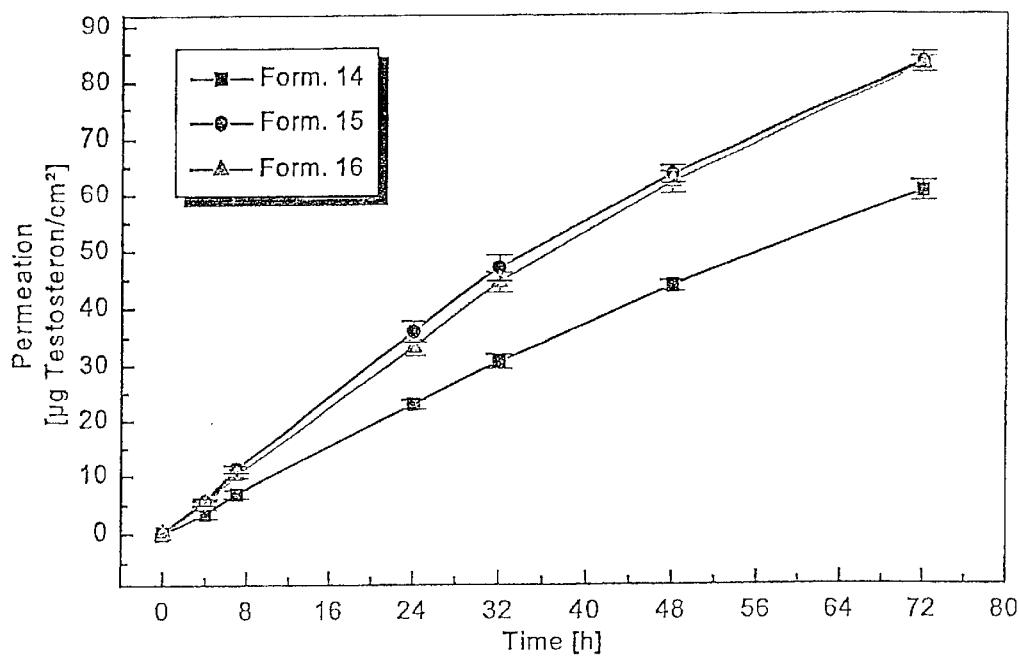
FIG. 6 is a graph showing the permeation of testosterone.

FIG. 6 shows the effect of the neutralization of the pressure-sensitive adhesive on the release of a neutral active substance. Here, too, one can see a marked increase in the release rates due to neutralization. In contrast to the basic active agents examined there obviously exists no linear dependence of the release rate on the neutralization degree.

What is claimed is:

1. A transdermal therapeutic system, which comprises:
   at least one pharmaceutical active agent selected from the group consisting of basic pharmaceutical active agents and neutral pharmaceutical active agents; and
   a pressure-sensitive adhesive comprising a polyacrylate polymer, wherein said polyacrylate polymer has a polyacrylate backbone containing monomer units selected from the group consisting of acrylic acid, methacrylic acid and ester derivatives of acrylic or methacrylic acid, and said monomer units comprise at least 50% (w/w) relative to a mean polymer mass of said polyacrylate polymer,
   a total amount of monomers selected from the group consisting of non-esterified acrylic acid and non-esterified methacrylic acid is 0.5 to 10.0% (w/w) relative to the mean polymer mass of said polyacrylate polymer, and
   the carboxyl groups of said non-esterified acrylic and methacrylic acid monomers are present stoichiometrically at 5 to 100% in the form of alkali salts or alkaline-earth salts, said salts being reaction products of a neutralization reaction of an alcoholic solution of an alkaline hydroxide or an alkaline-earth hydroxide with said acrylate polymer(s), or of a neutralization reaction of an alkali alcoholate or an alkaline-earth alcoholate with said acrylate polymer(s).

2. The transdermal therapeutic system according to claim 1, wherein said system is a matrix system comprising a non-adhesive backing layer, one to three layer(s) comprising said pressure sensitive adhesive, and a removable adhesive protective layer.

3. The transdermal therapeutic system according to claim 1, wherein the alkali salt is the sodium or potassium salt.

4. The transdermal therapeutic system according to claim 1, wherein the alkaline earth metal is the magnesium or calcium salt.

5. The transdermal therapeutic system according to claim 1, wherein the pharmaceutical active substance is present, at 20° C., as a liquid.

6. The transdermal therapeutic system according to claim 5, wherein the pharmaceutical active agent is present in an amount from 2 to 50% (m/m), relative to the active substance-containing matrix.

7. The transdermal therapeutic system according to claim 1, wherein said system contains a basic pharmaceutical active substance in the form of a pharmaceutically acceptable salt.

8. The transdermal therapeutic system according to claim 1, wherein the carboxyl group-containing polymer is crosslinked with aluminium ions in a concentration of 0.005 to 0.5% (m/m) calculated as aluminium, relative to the polymer mass.

9. The transdermal therapeutic system according to claim 8, wherein the crosslinking reagent utilised is aluminum acetyl acetonate.

10. The transdermal therapeutic system according to claim 1, wherein the active substance-containing matrix contains at least one enhancer from the group of straight-chain or branched-chain fatty alcohols of the general formula $C_xH_yCH_2OH$ where X=9 to 17 and Y=19 to 33, or the matrix contains at least one enhancer selected from the group consisting of decanol, dodecanol, 2-hexyl decanol, 2-octyl dodecanol and oleyl alcohol.

11. The transdermal therapeutic system according to claim 1, wherein the active substance-containing matrix has a content of at least one enhancer from the group of saturated or unsaturated fatty acids of the general formula $C_xH_y$COOH where X=9 to 17 and Y=19 to 33 or the matrix contains at least one enhancer selected from the group consisting of undecylenic acid, lauric acid, myristic acid and oleic acid.

12. The transdermal therapeutic system according to claim 1, wherein the active substance-containing matrix contains at least one enhancer from the group of fatty acid esters or of their derivatives obtained by ethoxylation which may each be present etherified with 5 to 20 molecules of ethylene oxide per sorbitan ester molecule.

13. The transdermal therapeutic system according to claim 1, wherein the active substance-containing matrix contains at least one enhancer from the group of fatty alcohol ethoxylates or the matrix contains at least one enhancer selected from the reaction products of dodecanol or oleyl alcohol with 1 to 5 units of ethylene oxide.

14. The transdermal therapeutic system according to claim 1, wherein the active substance-containing matrix contains at least one enhancer from the group of esters of fatty acids with methanol, ethanol or isopropanol or the matrix contains at least one enhancer selected from the group consisting of methyl laurate, ethyl oleate, isopropyl myristate and isopropyl palmitate.

15. The transdermal therapeutic system according to claim 1, wherein the active substance-containing matrix contains at least one enhancer from the group of esters of fatty alcohols with acetic acid or lactic acid or the matrix contains at least one enhancer selected from the group consisting of lauryl lactate and oleyl acetate.

16. The transdermal therapeutic system according to claim 1, wherein the active substance-containing matrix contains at least one water-miscible enhancer from the group of polyvalent aliphatic alcohols or polyethylene glycols, or the matrix contains at least one water-miscible enhancer selected from the group consisting of 1,2-propylene glycol, glycerol, 1,3-butanediol, dipropylene glycol and polyethylene glycols with mean molecular weights of 200 to 600 Da.

17. The transdermal therapeutic system according to claim 16, wherein said enhancer is present in the matrix dispersed partially or completely, as in an emulsion.

18. The transdermal therapeutic system according to claim 1, wherein the active substance-containing matrix has a content of at least one plasticizer selected from citric acid esters, saturated triglycerides, triethyl citrate, acetyl tributyl citrate, triacetin or medium-chain triglycerides with fatty acid chains having a length of 8 to 12 carbon atoms.

19. The transdermal therapeutic system according to claim 10, wherein the enhancer accounts for 10 to 80%, of the active substance-containing matrix.

20. The transdermal therapeutic system according to claim 1, wherein the system contains dispersed therein a water-adsorbing or water-absorbing solid agent in dry condition, or the system contains dispersed therein in dry condition a water-absorbing solid agent selected from the group consisting of sodium or calcium salts of carboxymethyl cellulose, crosslinked polyvinylpyrrolidone, sodium or calcium salts of crosslinked polyacrylic acid or polymethacrylic acid, and sodium or calcium salts of carboxymethyl starch.

21. The transdermal therapeutic system according to claim 1, wherein there is provided a separate layer which is pressure-sensitive adhesive on the skin-facing side which comprises a carboxyl group-containing pressure-sensitive acrylate adhesive the carboxyl groups of which are not present as a salt or said adhesive comprises a carboxyl group-containing pressure-sensitive acrylate adhesive the carboxyl groups of which are not present as a salt which is crosslinked by aluminum ions.

22. The transdermal therapeutic system according to claim 1, wherein there is provided a separate layer which is pressure-sensitive adhesive on the skin-facing side and comprises a carboxyl group-free and hydroxyl group-containing pressure-sensitive acrylate adhesive or comprises a carboxyl group-free and hydroxyl group-containing pressure-sensitive acrylate adhesive which is crosslinked by aluminium ions or titanium ions.

23. The transdermal therapeutic system according to claim 1, wherein the system contains a separate layer which is pressure-sensitive adhesive on the skin-facing side and comprises a silicone-based pressure-sensitive adhesive.

24. The transdermal therapeutic system according to claim 1, wherein there is provided a separate layer which is pressure-sensitive adhesive on the skin-facing side and comprises a pressure-sensitive adhesive containing a mixture of polyisobutylenes having at least two different medium molecular weights.

25. The transdermal therapeutic system according to claim 21, wherein said layer, which is pressure-sensitive adhesive on the skin-facing side, has a weight per unit area of 10 to 100 $g/m^2$.

26. The transdermal therapeutic system according to claim 1, wherein the pharmaceutical active substance is nicotine, xanomeline or rivastigmin.

27. The transdermal therapeutic system according to claim 1, wherein the pharmaceutical active substance is a steroid hormone.

28. The transdermal therapeutic system according to claim 1, wherein the pharmaceutical active agent is an organic ester of nitric acid.

29. The transdermal therapeutic system according to claim 1, said adhesives being water-insoluble or not dispersible in water.

30. The transdermal therapeutic system according to claim 1, wherein the carboxyl groups of said non-esterified acid monomers are present stoichiometrically at 10 to 50% in the form of alkali salts or alkaline-earth salts.

31. The transdermal therapeutic system according to claim 1, wherein said salts are the reaction product of a neutralization reaction of an alcoholic solution of sodium hydroxide or potassium hydroxide with said polyacrylate polymer(s).

32. A method for the manufacture of a transdermal therapeutic system, comprising the steps of:

providing a solution of a pressure-sensitive adhesive in organic solvent(s), wherein said adhesive comprises a polyacrylate polymer, the polyacrylate backbone of said adhesive containing monomer units selected from the group consisting of acrylic acid, methacrylic acid and ester derivatives of the aforementioned acids, and wherein said monomers amount to at least 50% (w/w), relative to the mean polymer mass of said polyacrylate polymer, and wherein the total amount of monomers selected from the group of non-esterified acrylic acid and non-esterified methacrylic acid is 0.5 to 10.0% (w/w), relative to the mean polymer mass of said polyacrylate polymer;

adding to said solution a neutralizing reagent selected from the group consisting of alcoholic solutions of alkali hydroxides of alcoholic solutions of alkaline-earth hydroxides, alkali alcoholates, and alkaline-earth alcoholates;

adding to said solution at least one pharmaceutical active agent selected from the group consisting of basic pharmaceutical active agents and neutral pharmaceutical active agents; and coating said solution onto a carrier film.

33. The method in accordance with claim 32, wherein said neutralizing agent is added at an amount which produces a degree of neutralization between 5 and 100%.

* * * * *